United States Patent
Kwok et al.

(10) Patent No.: US 8,426,216 B2
(45) Date of Patent: *Apr. 23, 2013

(54) METHODS FOR AUTHENTICATING ARTICLES WITH OPTICAL REPORTERS

(75) Inventors: Thomas Kwok, Miller Place, NY (US); Ming-Hwa Liang, Stony Brook, NY (US); Stephane Shu Kin So, Middle Island, NY (US)

(73) Assignee: APDN (B.V.I.), Inc., Stony Brook, NY (US)

( * ) Notice: Subject to any disclaimer, the term of this patent is extended or adjusted under 35 U.S.C. 154(b) by 621 days.

This patent is subject to a terminal disclaimer.

(21) Appl. No.: 11/954,038

(22) Filed: Dec. 11, 2007

(65) Prior Publication Data

US 2008/0299559 A1    Dec. 4, 2008

Related U.S. Application Data

(63) Continuation-in-part of application No. 11/437,265, filed on May 19, 2006, which is a continuation-in-part of application No. 10/825,968, filed on Apr. 15, 2004.

(60) Provisional application No. 60/682,976, filed on May 20, 2005, provisional application No. 60/463,215, filed on Apr. 16, 2003, provisional application No. 60/874,425, filed on Dec. 12, 2006, provisional application No. 60/877,875, filed on Dec. 29, 2006, provisional application No. 60/877,869, filed on Dec. 29, 2006.

(51) Int. Cl.
*C12Q 1/68* (2006.01)
*C12Q 1/00* (2006.01)

(52) U.S. Cl.
USPC ............... 436/164; 436/91; 436/94; 252/582; 435/6.11; 442/121

(58) Field of Classification Search .................... 436/91, 436/94, 164; 252/582; 435/6.11; 442/121
See application file for complete search history.

(56) References Cited

U.S. PATENT DOCUMENTS 4,183,989 A    1/1980   Tooth
4,739,044 A    4/1988   Stabinsky
(Continued)

FOREIGN PATENT DOCUMENTS

EP    1403333 A1    3/2004
GB    243570 A     8/2007
(Continued)

OTHER PUBLICATIONS

Wollenberger, L.V. Detection of DNA using upconverting phosphor reporter probes.(1997). Proceedings of SPIE—The International Society for Optical Engineering, 2895(Ultrasensitve Biochemical Diagnostics II), 100-111.*

(Continued)

*Primary Examiner* — Krishnan S Menon
*Assistant Examiner* — Rebecca M Fritchman
(74) *Attorney, Agent, or Firm* — Algis Anilionis; F. Chau & Associates LLC (57) ABSTRACT

This invention pertains to methods for authenticating an article comprising tagging the article with light emitting optical reporter particles, and more specifically tagging the articles with up-converting phosphor particles (UCP), linked to nucleic acids of detectable sequence.

34 Claims, 2 Drawing Sheets

U.S. PATENT DOCUMENTS

| | | | |
|---|---|---|---|
| 4,757,141 | A | 7/1988 | Fung et al. |
| 5,047,519 | A | 9/1991 | Hobbs, Jr. et al. |
| 5,132,242 | A | 7/1992 | Cheung |
| 5,139,812 | A | 8/1992 | Lebacq |
| 5,151,507 | A | 9/1992 | Hobbs, Jr. et al. |
| 5,429,952 | A | 7/1995 | Garner et al. |
| 5,602,381 | A | 2/1997 | Hoshino et al. |
| 5,639,603 | A | 6/1997 | Dower et al. |
| 5,763,176 | A | 6/1998 | Slater et al. |
| 5,776,713 | A | 7/1998 | Garner et al. |
| 5,866,336 | A | 2/1999 | Nazarenko et al. |
| 5,942,444 | A | 8/1999 | Rittenburg et al. |
| 5,989,823 | A | 11/1999 | Jayesana et al. |
| 6,030,657 | A | 2/2000 | Butland et al. |
| 6,057,370 | A | 5/2000 | Weiland et al. |
| 6,127,120 | A | 10/2000 | Graham et al. |
| 6,140,075 | A | 10/2000 | Russell et al. |
| 6,169,174 | B1 | 1/2001 | Hasewega et al. |
| 6,312,911 | B1 | 11/2001 | Bancroft et al. |
| 6,326,489 | B1 * | 12/2001 | Church et al. ............... 536/25.3 |
| 6,342,359 | B1 | 1/2002 | Lee et al. |
| 6,399,397 | B1 | 6/2002 | Zarling et al. |
| 6,576,422 | B1 | 6/2003 | Weinstein et al. |
| 6,686,149 | B1 | 2/2004 | Sanchis et al. |
| 6,743,640 | B2 | 6/2004 | Whitten et al. |
| 6,995,256 | B1 | 2/2006 | Li et al. |
| 7,060,874 | B2 | 6/2006 | Wilkins |
| 7,115,301 | B2 | 10/2006 | Sheu et al. |
| 7,160,996 | B1 | 1/2007 | Cook |
| 7,223,906 | B2 | 5/2007 | Davis |
| 2002/0048822 | A1 | 4/2002 | Rittenburg et al. |
| 2002/0056147 | A1* | 5/2002 | Dau et al. ........................ 800/8 |
| 2002/0187263 | A1 | 12/2002 | Sheu et al. |
| 2003/0142704 | A1 | 7/2003 | Lawandy |
| 2003/0142713 | A1 | 7/2003 | Lawandy |
| 2003/0162296 | A1 | 8/2003 | Lawandy |
| 2003/0177095 | A1 | 9/2003 | Zorab et al. |
| 2004/0063117 | A1 | 4/2004 | Rancien et al. |
| 2004/0166520 | A1 | 8/2004 | Connolly |
| 2004/0219287 | A1 | 11/2004 | Regan et al. |
| 2005/0059059 | A1 | 3/2005 | Liang |
| 2005/0214532 | A1 | 9/2005 | Kosak et al. |
| 2006/0017957 | A1 | 1/2006 | Degott et al. |
| 2006/0017959 | A1 | 1/2006 | Downer et al. |
| 2006/0117465 | A1 | 6/2006 | Willows et al. |
| 2006/0121181 | A1 | 6/2006 | Sleat et al. |
| 2006/0286569 | A1 | 12/2006 | Bar-Or et al. |
| 2007/0048761 | A1 | 3/2007 | Reep et al. |

FOREIGN PATENT DOCUMENTS

| | | |
|---|---|---|
| GB | 2434570 | 8/2007 |
| RU | 2170084 C1 | 10/2001 |
| WO | WO 87/06383 | 10/1987 |
| WO | WO 9014441 | 11/1990 |
| WO | WO 9502702 A1 | 1/1995 |
| WO | WO 9506249 | 3/1995 |
| WO | WO 97/45539 | 12/1997 |
| WO | WO 98/06084 A1 | 2/1998 |
| WO | WO 9959011 | 11/1999 |
| WO | WO 0055609 | 9/2000 |
| WO | WO 0125002 A1 | 4/2001 |
| WO | WO 0199063 A1 | 12/2001 |
| WO | WO 02057548 A1 | 7/2002 |
| WO | WO 02084617 A1 | 10/2002 |
| WO | WO 03/030129 A2 | 4/2003 |
| WO | WO 03080931 A1 | 10/2003 |
| WO | WO 2004/025562 A1 | 3/2004 |
| WO | WO 2004025562 A1 | 3/2004 |

OTHER PUBLICATIONS

Van De Rijke, et al. "Up-converting phosphor reporters for nucleic acid microarrays." Nature Biotechnology, vol. 19, pp. 273-276 (2001). Nature Publishing Group, New York.

Corstjens, et al. "Infrared up-converting phosphors for bioassays." IEE Proceedings—Nanobiotechnology, vol. 152, pp. 64-72 (2005). Institution of Engineering and Technology, London.

Heid, et al. "Real Time Quantitative PCR." Genome Research, vol. 6, pp. 986-994 (1996). Cold Spring Harbor Laboratory Press, Woodbury, New York.

Tyagi & Kramer. "Molecular Beacons: probes that Fluoresce upon Hybridization." Nature Biotechnology, vol. 14, pp. 303-308 (1996). Nature Publishing Group, New York.

Lee, et al. "Allelic discrimination by nick-translation PCR with fluorogenic probes." Nucleic Acids Research, vol. 21, pp. 3761-3766 (1993). Oxford University Press, Oxford, England.

Tyagi, et al. "Multicolor molecular beacons for allele discrimination." Nature Biotechnology, vol. 16, pp. 49-53 (1997). Nature Publishing Group, New York.

Versalift, "Market Growth: the evolution of the aerial lift industry," Oct. 1, 2002, Accessed on web Nov. 10, 2008.

Schultz et al., "Archived or directly swabbed latent fingerprints as a DNA source for STR typing," Forensic Science International, 127 (2002) 128-130.

Zuckermann, et al. "Efficient methods for attachment of thiol specific probes to the 3'- ends of synthetic oligodeoxyribonucleotides," Nucleic Acids Research, vol. 15, pp. 5305-5321 (1987), IRL Press Limited, Oxford England.

Whitcombe, et al. "Detection of PCR products using self-probing amplicons and fluorescence," Nature Biotechnology, vol. 17, pp. 804-807 (1999), Nature America, Inc., New York.

Nazarenko, et al. "A closed tube format for amplification and detection of DNA based on energy transfer," Nucleic Acids Research, vol. 25, pp. 2516-2521 (1997), Oxford University Press.

Sproat, et al. "The synthesis of protected 5'-mercapto-2', 5'-dideoxyribonucleoside-3-O-phosphoramidites, uses of 5'-mercapto-oligodeoxyribonucleotides," Nucleic Acids Research, vol. 15, pp. 4837-4848 (1987), IRL Press Limited, Oxford, England.

Nelson, et al. "Bifunctional oligonucleotide probes synthesized using a novel CPG support are able to detect single base pair mutations," Nucleic Acids Research, vol. 17, pp. 7187-7194 (1989), IRL Press Limited, Oxford, England.

Gupta, et al. "A general method for the synthesis of 3'-sulfhydryl and phosphate group containing oligonucleotides," Nucleic Acids Research, vol. 19, pp. 3019-3025 (1991) Oxford University Press, Oxford, England.

Holland, et al. "Detection of specific polymerase chain reacton product by utilizing the 5'[to] 3'exonuclease activity of Thermus aquaticus DNA polymerase," Proceedings of the National Academy of Sciences, vol. 88, pp. 7276-7280 (1991), National Academy of Sciences, Washington, DC.

Gibson, et al. "A Novel Method for Real Time Quantitative RT-PCR," Genome Research, vol. 6, pp. 995-1001 (1996) Cold Spring Harbor Laboratory Press, Woodbury, NY.

Agrawal & Tang, "Site-specific functionalization of oligodeoxynucleotides for non-radioactive labeling," Tetrahedon Letters, vol. 31, pp. 1542-1546 (1990), Pergamon Press, Great Briton.

Hussein et al. "Molecular Characterization of Cotton Genotypes Using PCR-based Markers," Journal of Applied Sciences Research 3(10): 1156-1159 (2007).

Jiang et al. "Polyploid formation created unique avenues for response to selection in *Gossypium* (cotton)," Proceedings of the National Academy of Sciences, USA, vol. 95, pp. 4419-4424, Apr. 1995.

Lee et al. "The complete chloroplast genome sequence of *Gossypium hirsutum*, organization and phylogenetic relationships to other angiosperms," BMC Genomics 7:61, Mar. 2006.

Ibrahim et al. "Complete nucleotide Sequence of the Cotton (*Gossypium barbadense* L.) Chloroplast Genome with a Comparative Analysis of sequence among 9 Dicot Plants," Genes and Genetic Systems vol. 81, pp. 311-321.

* cited by examiner

SEQUENCE LISTING

```
<160> NUMBER OF SEQ ID NOS: 2

<210> SEQ ID NO 1
<211> LENGTH: 24
<212> TYPE: DNA
<213> ORGANISM: Unknown
<220> FEATURE:
<223> OTHER INFORMATION: primer  artificial sequence

<400> SEQUENCE: 1
cgccagggtt ttcccagtca cgac                                              24

<210> SEQ ID NO 2
<211> LENGTH: 17
<212> TYPE: DNA
<213> ORGANISM: Unknown
<220> FEATURE:
<223> OTHER INFORMATION: primer  artifical sequence

<400> SEQUENCE: 2
caggaaacag ctatgac                                                      17
```

METHODS FOR AUTHENTICATING ARTICLES WITH OPTICAL REPORTERS

CROSS REFERENCE

This application is a continuation-in-part of patent application Ser. No. 11/437,265 having a filing date of May 19, 2006 that is related to provisional patent application 60/682,976 filed on May 20, 2005; this application is also a continuation-in-part of patent application Ser. No. 10/825,968 having a filing date of Apr. 15, 2004 that is related to provisional patent application 60/463,215 filed on Apr. 16, 2003; this application is also related to provisional patent application 60/874,425 having a filing date of Dec. 12, 2006; this application is also related to provisional patent application 60/877,875 having a filing date of Dec. 29, 2006; this application is also related to provisional patent application 60/877,869 having a filing date of Dec. 29, 2006; each of the patent applications being hereby incorporated by reference including patent application Ser. No. 11/954,009 now issued as U.S. Pat. No. 8,124,333; Ser. No. 11/954,030 now issued as U.S. Pat. No. 8,372,648; Ser. No. 11/954,044; Ser. No. 11/954,051 and Ser. No. 11/954,055; each of which were co-filed with the present application on Dec. 11, 2007.

FIELD

This invention pertains to methods for authenticating articles by tagging or labeling the articles with optical reporter particles, and more specifically to methods for tagging the articles with up-converting phosphor particles (UCP) having nucleic acids of detectable sequence.

BACKGROUND

Optical reporters such as fluorescent dyes and upconverting phosphors have been used to detect the presence of biomolecules such as proteins and DNA molecules. Up-converting phosphor particles (UCP) have been encapsulated in transparent polyacrylate micro-carriers which can bond with protein sensors via functional groups as described in U.S. Pat. No. 5,132,242. Silylation techniques have also been utilized for binding antibodies to UCPs. Biotin/avidin binding has been utilized to detect biotinylated deoxyribonucleic acid (DNA) by UCP particles with avidin molecules on their surfaces. Hapten/digoxigenin sandwich technology has also been used to indirectly detect the presence of DNA with modified UCP particles.

Heretofore, the covalent binding of UCP particles to DNA molecules of detectable sequence has not been known. Such particles would be useful for labeling and authenticating articles and materials. Thus, there is accordingly a need for methods for authenticating articles, where the methods utilize compositions comprising a light emitting up-converting phosphor particle linked to a sequenceable DNA molecule. The present invention satisfies these needs as well as others.

SUMMARY

This invention relates to methods for authenticating articles that utilize compositions which link biomolecules to visual or machine-detectable reporters. The methods of authentication comprise placing, associating, or integrating an optical reporter taggant with the article of interest. The optical reporters can be easily detected by using a high energy light source for excitation, with the location of labeled biomolecules identified by the presence of an optical reporter. The location and emission wavelength of the optical reporters provides a first level of security or authentication of the tagged article of interest. After the location of the optical reporters and associated biomolecules on the article has been determined, the biomolecules may be characterized and identified to further increase the level of security and/or authenticity of the article. When the biomolecule attached to the optical reporter is a DNA molecule, PCR or sequence analysis techniques can be utilized to further authenticate the article.

In many embodiments of the method for authenticating and article comprises the steps of;

providing an optical reporter marker, the optical reporter marker having at least one light emitting upconverting phosphor particle linked to at least one nucleic acid taggant, the nucleic acid taggant having an identifiable portion, introducing the optical reporter marker to the article of interest, detecting the optical reporter marker associated with the article of interest with a light source, obtaining or collecting a sample of the optical reporter marker from the article of interest for analysis; and analyzing the collected sample to detect the presence of the identifiable portion of the nucleic acid taggant linked to the upconverting phosphor particle. In many embodiments the analyzing of the collected sample comprises determining the DNA sequence of the nucleic acid taggant, and comparing the determined DNA sequence with a known or reference DNA sequence.

In some embodiments, the optical reporter marker provided in the methods of the invention comprises a composition of the formula I:

(cOpR)-[L-(NA)]$_m$  I wherein: m is an integer greater than 1, (cOpR) is a coated optical reporter particle, (NA) is a nucleic acid oligomer of detectable sequence and L is a linking group covalently bound to the coated optical reporter particle and to the nucleic acid oligomer.

The (cOpR) of the composition may comprise an upconverting phosphor (UCP) material coated with silica. Where the compositions are coated with silica, the silica comprises at least one Si—O bond.

The (NA) of the composition may be a single or double stranded DNA molecule having a length of between about 40 base pairs and about 1000 base pairs.

The linker L of the composition may comprise an alkylene moiety having a first end covalently bound to the coated optical reporter particle and a second end covalently bound to the nucleic acid oligomer.

Where the composition utilized in the methods of the invention comprises a (UCP), in certain embodiments, the (UCP) is an upconverting phosphor particle of the formula:

Y$_x$Yb$_y$Er$_z$O$_2$S; or

Na(Y$_x$Yb$_y$Er$_z$)F$_4$;

wherein:
x is from about 0.6 to about 0.95;
y is from about 0.05 to about 0.35; and
z is from about 0.1 to about 0.001.

In other embodiments, the linker L may be of the formula:

-A-R$^1$—B— where R$^1$ is C$_{2-8}$alkylene, -A- is a group covalently bonded to the surface of the coated optical reporter and —B— is a group covalently bonded to the 3' or 5' end of the nucleic acid oligomer.

In other embodiments, a composition used in the methods for authenticating and article of the invention has the formula:

where m is an integer greater than 1; UCP is an upconverting phosphor particle; DNA is a single or double stranded deoxyribonucleic acid oligomer; $R^1$ is $C_{2-8}$alkylene; -A- is a group capable of covalently bonding to the surface of the upconverting phosphor particle and —B— is a group capable of bonding to the 3' or 5' end of the deoxyribonucleic acid oligomer.

All patents and publications identified herein are incorporated herein by reference in their entirety.

DESCRIPTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl" means a moiety of the formula —R'—R"—R'" where R' is alkylene, R" is —$SO_2$— and R'" is alkyl as defined herein.

"Amino means a moiety of the formula —NR—R' wherein R and R' each independently is hydrogen or alkyl.

"Alkylsulfanyl" means a moiety of the formula —SR wherein R is alkyl as defined herein.

"Urea" or means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —$SO_2$—NR'R" wherein R', R" and R'" each independently is hydrogen or alkyl.

"Optionally substituted", when used in association with "aryl", phenyl", "heteroaryl" "cycloalkyl" or "heterocyclyl", means an aryl, phenyl, heteroaryl, cycloalkyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR, —$SO_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Optional" or "optionally" means that the subsequently described event or circumstance may but need not occur, and that the description includes instances where the event or circumstance occurs and instances in which it does not.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The terms "those defined above" and "those defined herein" when referring to a variable incorporates by reference the broad definition of the variable as well as preferred, more preferred and most preferred definitions, if any.

The term "emitting reporter" means a chemical substituent or material that produces, under appropriate excitation conditions, a detectable optical signal. The optical signal produced by an emitting reporter is typically electromagnetic radiation in the near-infrared, visible, or ultraviolet portions of the spectrum. The emitting reporters of the invention are generally up-converting reporters, but can also be for example, fluorescent and colorimetric substituents.

The term "phosphor particle" means a particle or composition comprising at least one type of upconverting phosphor material.

The term "primer" means a nucleotide with a specific nucleotide sequence which is sufficiently complimentary to a particular sequence of a target DNA molecule, such that the primer specifically hybridizes to the target DNA molecule.

The term "probe" refers to a binding component which binds preferentially to one or more targets (e.g., antigenic epitopes, polynucleotide sequences, macromolecular receptors) with an affinity sufficient to permit discrimination of labeled probe bound to target from nonspecifically bound labeled probe (i.e., background).

The term "probe polynucleotide" means a polynucleotide that specifically hybridizes to a predetermined target polynucleotide.

The term "oligomer" refers to a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "PCR" refers to polymerase chain reaction. This refers to any technology where a nucleotide is amplified via a temperature cycling techniques in the presence of a nucleotide polymerase, preferably a DNA polymerase. This includes but is not limited to real-time PCR technology, reverse transcriptase-PCR, and standard PCR methods.

The term "nucleic acid" means a polymer composed of nucleotides, e.g. deoxyribonucleotides or ribonucleotides, or compounds produced synthetically which can hybridize with naturally occurring nucleic acids in a sequence specific manner analogous to that of two naturally occurring nucleic acids, e.g., can participate in hybridization reactions, i.e., cooperative interactions through Pi electrons stacking and hydrogen bonds, such as Watson-Crick base pairing interactions, Wobble interactions, etc.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "polynucleotide" or "nucleotide" refer to single or double stranded polymer composed of nucleotide monomers of generally greater than 50 nucleotides in length.

The term "monomer" as used herein refers to a chemical entity that can be covalently linked to one or more other such entities to form an oligomer. Examples of "monomers" include nucleotides, amino acids, saccharides, peptides, and the like. The term nucleotide means The term "linker" means a compound or a composition which covalently links a biomolecule to the surface of a coated emitting reporter. For example, but not limited to a silyinated coated upconverting phosphor particle linked to a DNA molecule.

The term "identifiable sequence" or "detectable sequence" means a nucleotide sequence which can by detected by hybridization and/or PCR technology by a primer or probe designed for specific interaction with the target nucleotide sequence to be identified. The interaction of the target nucleotide sequence with the specific probe or primer can be detected by optical and/or visual means to determine the presence of the target nucleotide sequence.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.5. Any open valency appearing on a carbon, oxygen sulfur or nitrogen atom in the structures herein indicates the presence of a hydrogen atom unless indicated otherwise. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure.

Methods for Authenticating an Article

The present invention relates to methods for authenticating an article, by labeling the article with an optical reporter marker linked to a nucleic acid tag, detecting the optical reporter, and then characterizing or verifying the nucleic acid taggant associated with the article in an effective manner, by nucleic acid sequencing, genotyping or like techniques. The invention allows for verification of tagged articles in a manner that's helps prevent forgers counterfeit producers from substituting false or counterfeit goods in place of authentic items.

Figure 1:
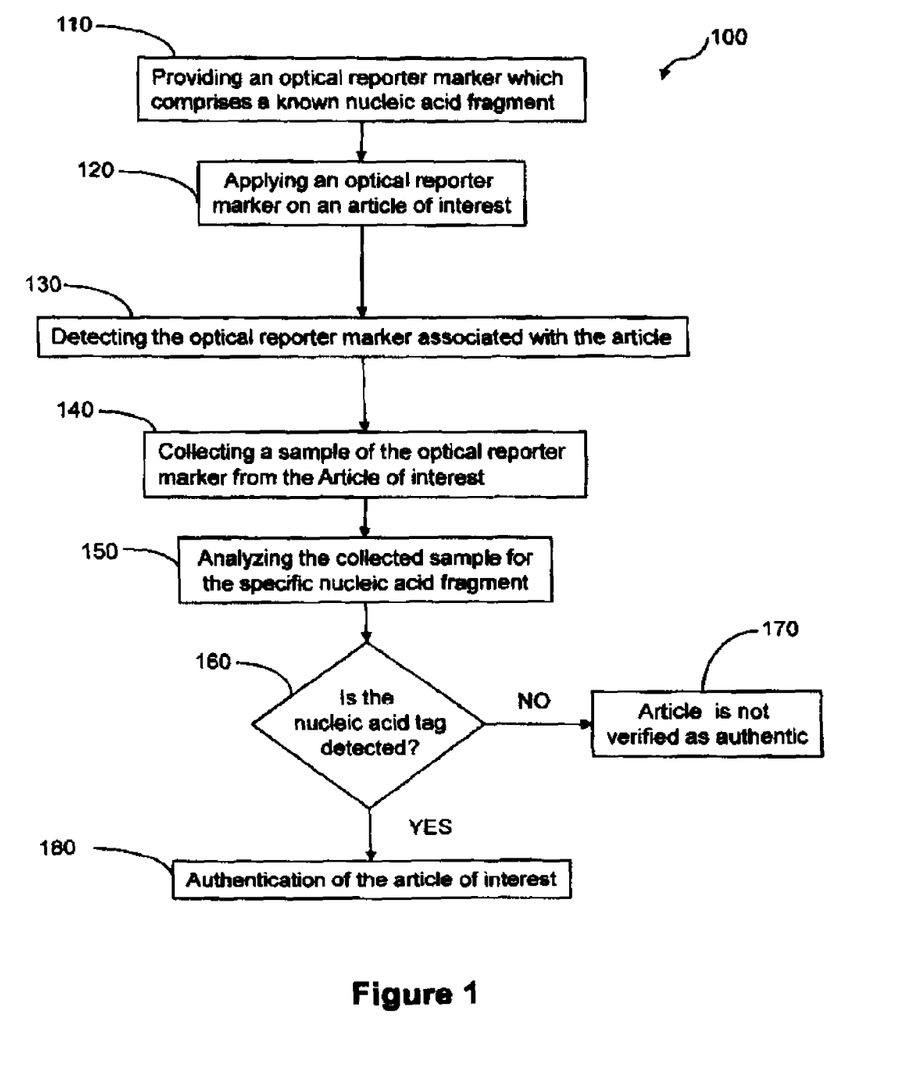
FIG. 1 is a flow chart of one embodiment of the methods for authenticating an article in accordance with the invention.

FIG. 1 is a flow chart illustrating generally a method 100 for authenticating an article with a nucleic acid-linked optical reporter marker in accordance with the invention. The method 100 comprises, at event 110, providing an optical reporter marker having a nucleic acid taggant linked to an optical reporter particle, the nucleic acid taggant having a known portion of its sequence identifiable or sequenceable.

The optical reporter particle of event 110 is a light emitting optical reporter and in most embodiments is an upconverting phosphor particle (UCP). In certain embodiments the upconverting phosphor particle UCP is coated with a silylination composition which is configured to covalently link to the nucleic acid taggant. Specific UCPs usable with the invention are described further below.

The nucleic acid (NA) taggant of event 110 may be DNA, cDNA, or any other nucleic acid fragment comprising nucleic acids or nucleic acid derivatives. The NA may be a nucleic acid fragment that is single stranded or preferably double stranded and may vary in length, depending on the article to be labeled as well as the detection technique utilized in the nucleic acid detection process.

The nucleic acid marker may be synthetically produced using a nucleic acid synthesizer or by isolating nucleic acid material from yeast, human cell lines, bacteria, animals, plants and the like. In certain embodiments, the nucleic acid material may be treated with restriction enzymes and then purified to produce an acceptable nucleic acid marker(s). The length of the nucleic acid tag usually ranges between about 50 to about 1 kilo bases, more usually about 100 bases to about 800 bases, and preferably 150 bases to about 500 b in length.

The nucleic acid taggant may comprise one specific nucleic acid sequence or alternatively, may comprise a plurality of various nucleic acid sequences. In one embodiment, polymorphic DNA fragments of the type short tandem repeats (STR) or single nucleotide polymorphisms (SNP) are utilized as an anti-counterfeit nucleic acid tag. While the use of a single sequence for a nucleic acid marker may make detection of the marker easier and quicker, the use of a plurality of nucleic acid sequences such as STR and SNP, in general, give a higher degree of security against forgers.

In certain embodiments of the methods of the invention, the nucleic acid taggant is derived from DNA extracted from a specific plant source and is specifically digested and ligated to generate artificial nucleic acid sequences which are unique to the world. The digestion and ligation of the extracted DNA is completed by standard restriction digestion and ligase techniques known to those skilled in the art of molecular biology.

The optical reporter marker compound may be produced as a solid or liquid, water or oil based, a suspension, an aggregate or the like. The optical reporter marker allows for easy detection of where the optical reporter marker is located on or within the article of interest with basic high intensity light emitting equipment such as a hand-held ultraviolet (UV) lamp, IR emitting diode, hand-held IR laser and the like.

The optical reporter marker also enables the authentication of the article of interest by both confirming that the correct emission spectra/wavelength for the optical reporter particle is detected as well as being able to locate and determine by sequencing if the nucleic acid taggant comprises the correct nucleic acid sequence.

In certain embodiments, the optical reporter marker may camouflage or "hide" a specified nucleic acid tag of verifiable sequence by including extraneous and nonspecific nucleic acid oligomers/fragments, thus making it difficult for unauthorized individuals such as forgers to identify the sequence of the nucleic acid tag. In certain embodiments, the optical reporter marker comprises a specified dsDNA taggant from a known source (i.e. mammal, invertebrate, plant and the like) along with genomic DNA from the corresponding or similar DNA source. The amount of the DNA taggant found in a optical reporter marker compound may vary depending on the article to be authenticated, the duration or shelf-life the taggant needs to be viable (e.g. 1 day, 1 month, 1 year, multiple years) prior to authentication, expected environmental exposure, the detection method to be utilized, and other factors.

The method 100 for authenticating an article further comprises, in event 120, applying or introducing the nucleic acid-linked optical reporter marker to an article of interest in event. The nucleic acid-linked optical reporter marker may be applied in a specific, pre-determined amount or quantity. The article may be labeled with an optical reporter marker throughout the complete article, as a coating over the entire article, or only in a predetermined region or portion of the article. The marker may be applied in liquid solution, liquid dispersion, paste, powder, or other form. Application of the marker may be carried out using an eye-dropper, spoon, spatula, syringe, or other applicator tool. When the article to be authenticated is a solid, a specified amount of optical reporter marker may be incorporated throughout the volume of the article, or only on the surface of the article or, in some embodiments, placed only on a previously designated section or portion of the article. In embodiments where the article to be authenticated is a fungible powder, the nucleic acid-lined optical reporter may be dispersed throughout the powdered material.

If the article is a textile or garment item, the marker could be either solid or liquid and applied to a predetermined area of the garment. Textiles may have a label with the manufactures name on it and may also be used as a region of the garment which the optical reporter marker is placed. The marker may be introduced, for example, by applying a liquid solution or suspension of the marker onto a selected portion of the garment and allowing the solution or suspension to dry by solvent evaporation to leave the markers in place. The marker can also be introduced by applying a binding solution containing DNA marker to the garment.

The authentication method 100 further comprises, in event 130, detecting the nucleic acid-linked optical reporter tag associated with the article of interest. Usually the detecting of the optical reporter marker associated with the article occurs after a period of time has lapsed. For example, after tagging the marked article may be introduced into a supply chain or the article may be placed into service. Frequently, forgers have the best access to articles when they are being shipped from the manufacturer/producer to a retail outlet or location. Forgers also have access to the articles of interest during maintenance or service of certain of products, such as aircraft, where the article of interest is inspected or replaced (i.e. fasteners). Having a method in which the producer can track and authenticate articles or goods allows for a better monitoring of when and where counterfeit goods are being replaced with forgeries or otherwise being tampered with.

Detecting the optical reporter particle(s) represents a first level of authentication of the article. When the optical reporter particle is an upconverting phosphor particle, the marker can be detected by a high energy invisible light source such as an infrared laser, which may be hand-held and manipulated by a user, or suitably mounted to allow goods to be positioned in the lamp output. The infrared light is absorbed by the optical reporter particles, which in turn emit light at a wavelength that is characteristic of the optical reporter particle. Various upconverting phosphor compositions that provide selectable output wavelengths are known in the art, as described further below, and may be used with the invention. Once the optical reporter has been located within or on the article of interest, obtaining a sample of the optical reporter marker may occur at event 140.

In event 140, a sample is collected from the article of interest having the optical reporter marker. In certain embodiments, this may comprise visually inspecting the marker compound found in event 130, and/or scraping, cutting or dissolving a portion of the marked article to obtain a sample for analysis. When the article has entered a supply chain or has been in service, a manufacturer or an authorized individual can collect a sample of the optical reporter marker from the article at any desired point along the supply chain or during the service or routine maintenance of an item where the article is utilized for authentication purposes. The collecting of the sample may be carried out, for example, by wiping the article with a cloth (which may be moistened with solvent) to remove the marker from the article. The sample collecting in other embodiments may be achieved using a cutting, gouging, scraping, abrading, or other sampling tool configured to remove a portion of the article containing the optical reporter marker.

The embodiment of FIG. 1 further comprises analyzing the collected sample for the presence of the nucleic acid taggant in event 150. In many embodiments the analyzing of the collected sample comprises determining the DNA sequence of the nucleic acid taggant, and comparing the determined DNA sequence with a known or reference DNA sequence. The analysis of the sample collected from the article may occur without further purification, but in many embodiments some form of extraction, isolation or purification of the nucleic acid tag obtained in the sample may be required. Details on the extraction, concentration and purification techniques useful for the methods of the invention are described more fully below and also in the examples.

In general, analyzing the sample comprises providing a "detection molecule" configured to the nucleic acid tag. A detection molecule includes but is not limited to a nucleic acid probe and/or primer set which is complementary to at least a portion of the sequence of the nucleic acid taggant, or a dye label or color-producing molecule configured to bind and adhere to the nucleic acid taggant. The detection of the nucleic acid taggant may further comprise amplifying the nucleic acid taggant using PCR, with the detection molecule(s) being primers which specifically bind to a certain sequence of the nucleic acid taggant. When real time PCR is utilized in the analysis of the sample, an identifiable nucleotide probe may also be provided to enhance the detection of the nucleic acid taggant as well as provide semi-quantitative or fully quantitative authentication results. With the use of real time PCR, results from the analysis of the sample can be completed within 30 minutes to two hours, including extracting or purifying the nucleic acid taggant from the collected sample. Various embodiments of the invention may utilize a wide range of detection methods besides for PCR and real time PCR, such as DNA microarray, fluorescent probes, probes configured to molecules which allow for the detection of the nucleic acid tag when bound to the probe by Raman spectroscopy, Infrared spectroscopy or other spectroscopic techniques used by those skilled in the art of nucleic acid detection. The method utilized to detect the nucleic acid is dependent on the quantity of nucleic acid taggant associated with the optical reporter marker. When only a few copies of NA taggant are collected in the marker sample, high sensitivity techniques such as PCR may be preferable over fluorescent probes.

In event 160 the results of the analysis of the collected sample are reviewed and a query or determination is made as to whether or not the specific nucleic acid taggant was detected in the sample. If the nucleic acid taggant is not found or not detected in the collected sample of the article of interest at event 160, the conclusion at event 170 from the analysis is the that article is not authentic or has been tampered with. If the nucleic acid taggant is detected in the sample at event 160, then the article is verified in event 180 as being authentic.

If a determination is made in event 170 that an article is not authentic, a different, earlier point in the supply or commerce chain may be selected and events 130 through 160 may be repeated. Thus an article from an earlier point in the supply chain would be selected, the optical reporter marker detected, and a sample collected and analyzed. If it is again determined that the article is not authentic or has been otherwise tampered with, then events 130-160 may be repeated with an article selected from yet an earlier point in the supply chain. In this manner, the time and/or location of tampering or counterfeit substitute may be located.

In some embodiments, the quantity or concentration of the nucleic acid taggant within a collected sample can be determined and compared to the initial amount of nucleic acid taggant placed in the article to allow for the detection of fraud caused by diluting the article with inferior products by forgers. In general, such quantitative detection would further comprise, in event 150, providing an internal or external control to evaluate the efficiency of detection from one sample/analysis to the next. The efficiency of detection may be affected by many parameters such as, probe hybridization conditions, molecules or substances in the good which may interfere with detection, and/or primer integrity, enzyme quality, temperature variations for detection methods utilizing PCR. By providing a control, in the detection methods, any variable conditions can be normalized to obtain an accurate final concentration of the nucleic acid taggant in the article.

In certain embodiments a plurality of nucleic acid tags with varying sequences associated with a corresponding plurality of optical reporters may be used in labeling a single article. The different nucleic acid tags can be detected qualitatively by the plurality of optical reporters, each with a different emission wavelength linked to a unique sequenceable nucleic acid taggant.

Nucleic Acid Tag Extraction and Capture Methods

A variety of nucleic acid extraction solutions have been developed over the years for extracting nucleic acid sequences from a sample of interest. See, for example, Sambrook et al. (Eds.) Molecular Cloning, (1989) Cold Spring Harbor Press. Many such methods typically require one or more steps of, for example, a detergent-mediated step, a proteinase treatment step, a phenol and/or chloroform extraction step, and/or an alcohol precipitation step. Some nucleic acid extraction solutions may comprise an ethylene glycol-type reagent or an ethylene glycol derivative to increase the efficiency of nucleic acid extraction while other methods only use grinding and/or boiling the sample in water. Other methods, including solvent-based systems and sonication, could also be utilized in conjunction with other extraction methods.

In some embodiments, the authentication process may comprise, in event 140 or 150, capturing the nucleic acid taggant directly with a complementary hybridization probe attached to a solid support. In general, the methods for capturing the nucleic acid tag involve a material in a solid-phase interacting with reagents in the liquid phase. In certain aspects, the nucleic acid probe is attached to the solid phase. The nucleic acid probe can be in the solid phase such as immobilized on a solid support, through any one of a variety of well-known covalent linkages or non-covalent interactions. In certain aspects, the support may be comprised of insoluble materials, such as controlled pore glass, a glass plate or slide, polystyrene, acrylamide gel and activated dextran. In other aspects, the support has a rigid or semi-rigid character, and can be any shape, e.g. spherical, as in beads, rectangular, irregular particles, gels, microspheres, or substantially flat support. In some embodiments, it can be desirable to create an array of physically separate sequencing regions on the support with, for example, wells, raised regions, dimples, pins, trenches, rods, pins, inner or outer walls of cylinders, and the like. Other suitable support materials include, but are not limited to, agarose, polyacrylamide, polystyrene, polyacrylate, hydroxethylmethacrylate, polyamide, polyethylene, polyethyleneoxy, or copolymers and grafts of such. Other embodiments of solid-supports include small particles, non-porous surfaces, addressable arrays, vectors, plasmids, or polynucleotide-immobilizing media.

In the capturing of the nucleic acid tag, a nucleic acid probe can be attached to the solid support by covalent bonds, or other affinity interactions, to chemically reactive functionality on the solid-supports. The nucleic acid can be attached to solid-supports at their 3', 5', sugar, or nucleobase sites. In certain embodiments, the 3' site for attachment via a linker to the support is preferred due to the many options available for stable or selectively cleavable linkers. Immobilization may be accomplished by a covalent linkage between the support and the nucleic acid. The linkage unit, or linker, is designed to be stable and facilitate accessibility of the immobilized nucleic acid to its sequence complement. Alternatively, non-covalent linkages such as between biotin and avidin or streptavidin may be used. Examples of other functional group linkers include ester, amide, carbamate, urea, sulfonate, ether, and thioester. A 5' or 3' biotinylated nucleotide can be immobilized on avidin or streptavidin bound to a support such as glass.

Depending on the initial concentration of the nucleic acid tag added to the article of interest, the tag can be detected quantitatively without being amplified by PCR. In some embodiments, a single stranded DNA tag labeled with a detection molecule (i.e. fluorophore, biotin, etc.) can be hybridized to a complementary probe attached to a solid support to allow for the specific detection of the "detection molecule" configured to the tag. The nucleic acid DNA tag can also be double stranded, with at least one strand being labeled with a detection molecule. With a dsDNA tag, the nucleic acid tag must be heated sufficiently and then quick cooled to produce single stranded DNA, where at least one of the strands configured with a detection molecule is capable of hybridizing to the complementary DNA probe under appropriate hybridization conditions.

In certain aspects of the invention, the complementary probe may be labeled with a detection molecule and allowed to hybridize to a strand of the nucleic acid tag. The hybridization of the probe can be completed within the good, when the good is a textile or can be completed after the nucleic acid tag/marker has been extracted from the good, such as when the goods are liquid (e.g. oil, gasoline, perfume, etc.). The direct detection methods described herein depend on having a large initial concentration of nucleic acid label embedded into the good or rigorous extraction/capture methods which concentrate the nucleic acid tag extracted from a large volume or mass of a particular article.

In some embodiments of the anti-counterfeit authentication process of the invention, real time PCR detection strategies may be used, including well known techniques such as intercalating dyes (ethidium bromide) and other double stranded DNA binding dyes used for detection (e.g. SYBR green, a highly sensitive fluorescent stain, FMC Bioproducts), dual fluorescent probes (Wittwer, C. et al., (1997) Bio-Techniques 22: 176-181) and panhandle fluorescent probes (i.e. molecular beacons; Tyagi S., and Kramer F R. (1996) Nature Biotechnology 14: 303-308). Although intercalating dyes and double stranded DNA binding dyes permit quantitation of PCR product accumulation in real time applications, they suffer from the previously mentioned lack of specificity, detecting primer dimer and any non-specific amplification product. Careful sample preparation and handling, as well as careful primer design, using known techniques must be practiced to minimize the presence of matrix and contaminant DNA and to prevent primer dimer formation. Appropriate PCR instrument analysis software and melting temperature analysis permit a means to extract specificity and may be used with these embodiments.

PCR amplification may be performed in the presence of a non-primer detectable probe which specifically binds the PCR amplification product, i.e., the amplified detector DNA moiety. PCR primers are designed according to known criteria and PCR may be conducted in commercially available instruments. The probe is preferably a DNA oligonucleotide specifically designed to bind to the amplified detector molecule. The probe preferably has a 5' reporter dye and a downstream 3' quencher dye covalently bonded to the probe which allows fluorescent resonance energy transfer. Suitable fluorescent reporter dyes include 6-carboxy-fluorescein (FAM), tetrachloro-6-carboxy-fluorescein (TET), 2,7-dimethoxy-4,5-dichloro-6-carboxy-fluorescein (JOE) and hexachloro-6-carboxy-fluorescein (HEX). A suitable reporter dye is 6-carboxy-tetramethyl-rhodamine (TAMRA). These dyes are commercially available from Perkin-Elmer, Philadelphia, Pa. Detection of the PCR amplification product may occur at each PCR amplification cycle. At any given cycle during the PCR amplification, the amount of PCR product is proportional to the initial number of template copies. The number of template copies is detectable by fluorescence of the reporter dye. When the probe is intact, the reporter dye is in proximity to the quencher dye which suppresses the reporter fluorescence. During PCR, the DNA polymerase cleaves the probe in the 5'-3' direction separating the reporter dye from the quencher dye increasing the fluorescence of the reporter dye which is no longer in proximity to the quencher dye. The increase in fluorescence is measured and is directly proportional to the amplification during PCR. This detection system is now commercially available as the TaqMan® PCR system from Perkin-Elmer, which allows real time PCR detection.

The methods of the invention are useful in producing compounds comprising biomolecules such as dsDNA, ssDNA, STR, SNP's as well a peptides and proteins, which are covalently bound to optical reporter particles.

The compounds of the invention are usable as authentication markers for various articles. For example, the compounds of the invention can be placed in or on such articles as clothing, paintings, documents, medicines, industrial solutions, computer components, explosives and the like. The compounds produced can also be utilized in micro array technology, as well as protein expression, genomic identification and other technologies utilizing DNA hybridization techniques.

Compounds utilized in the Methods of the Invention

The methods of authentication of an article of the invention comprise compounds of the formula I:

$$(cOpR)\text{-}[L\text{-}(NA)]_m$$

wherein:
m is an integer greater than 1;
(cOpR) is a coated optical reporter particle;
(NA) is a nucleic acid oligomer of detectable sequence; and
L is a linking group covalently bound to the coated optical reporter particle and to the nucleic acid oligomer.

While formula I specifically relates to linking nucleic acid oligomers or nucleotides to the surface of the coated optical reporter particle, it should be understood to the those skilled in the art that other biomolecules besides nucleotides can be covalently linked to L. Such biomolecules include but are not limited to peptides, proteins, antibodies, enzymes, DNA binding proteins and the like. These biomolecules, may be modified to include lipids, carbohydrates, fluorescent and/or upconverting phosphor molecules or other detectable compounds or markers.

In many embodiments, NA is a DNA oligomer. The DNA oligomer may be either single stranded DNA or double stranded DNA. In certain embodiments NA may be comprise cDNA, RNA, STR (single tandem repeat) or SNP (single nucleotide polymorphism). NA oligomers of the compositions of the invention may also be modified to comprise at least one dUTP nucleic acid or at least one nucleic acid within the oligomer which has been modified to contain a detectable marker.

In many embodiments NA is a DNA oligomer having a length of between about 40 base pairs and about 1000 base pairs (per strand).

In other embodiments the DNA has a length of between about 80 and 500 base pairs (per strand).

In yet other embodiments the DNA has a length of between about 100 to about 250 base pairs (per strand).

The DNA used with the invention may be natural or synthetically produced. All or a portion of the DNA may comprise an identifiable sequence.

In certain embodiments of formula I, the coated optical reporter comprises a visible or infrared detectable light emitting material selected from the group consisting of a fluorescent dye, an upconverting phosphor, a ceramic powder, or a quantum dot material. In most embodiments where the cOpR comprises a visible or infrared detectable light emitting material, the light emitting materials are excitable by UV, visible or an infrared light source.

In some embodiments, rare earth-doped ceramic particles are used as phosphor particles. Phosphor particles may be detected by any suitable method, including but not limited to up-converting phosphor technology (UPT), in which up-converting phosphors transfer lower energy infrared (IR) radiation into higher-energy visible light. Although an understanding of the mechanism is not necessary to practice the present invention and the present invention is not limited to any particular mechanism of action, in some embodiments the UPT up-converts infrared light to visible light by multi-photon absorption and subsequent emission of dopant-dependant phosphorescence (See, e.g., U.S. Pat. No. 6,399,397; van De Rijke, et al., Nature Biotechnol. 19(3):273-6 (2001); Corstjens, et al., IEE Proc. Nanobiotechnol. 152(2):64 (2005), each incorporated by reference herein in its entirety.

In many embodiments, the phosphor nanoparticles utilized in the methods of the invention may be of the formula A $$(Y_x RE^1{}_y RE^2{}_z)_2 O_3 \quad\quad A$$

wherein:

RE$^1$ and RE$^2$ each is a different rare earth element;

x is from about 0.6 to about 0.95;

y is from 0 to about 0.35; and z is from 0 0.1 to about 0.001;

provided that y and z are not simultaneously equal to 0.

The rare earth elements RE$^1$ and RE$^2$ may each independently be selected from Ytterbium, Erbium, Holmium, Thulium, or Terbium.

In many embodiments RE$^1$ is Ytterbium.

In many embodiments RE$^2$ is Erbium.

The up-converting particles utilized in the methods of the invention may be spherical, non-agglomerated, non-porous particles with an average size of 40-60 nm. In general, particle sizes may range from about 10 nm to about 5 um in size. Such up-converting phosphor nanopowders such as doped yttrium oxide and yttrium oxysulfide are commercially available and may be obtained from such as Nanocerox, Inc., of Ann Arbor, Mich.

Suitable examples of up-converting phosphors are compounds of rare earths or elements from the group IIIB such as: Na-yttrium fluoride, lanthanum fluoride, lanthanum oxysulphide, yttrium oxysulphide, yttrium fluoride, yttrium gallate, gadolinium fluoride, barium-yttrium fluorides, gadolinium oxysulphide as well as compounds of the above type doped with activator pairs such as ytterbium/erbium, ytterbium/thulium or ytterbium/holmium. Other suitable up-converting phosphors include chelate compounds of erbium, neodymium, thulium, holmium and praseodymium.

The following compositions are merely illustrative of some of the up-converting phosphor containing compositions that can be synthesized by the synthetic reaction schemes of the methods of the present invention. Various modifications to these synthetic reaction schemes can be made and will be suggested to one skilled in the art having referred to the disclosure contained in this Application.

TABLE I

Upconverting Phosphor Compositions

| Phosphor Material | Absorber Ion | Emitter Ion |
|---|---|---|
| Oxysulfides (O$_2$S) | | |
| Y$_2$O$_2$S | Ytterbium | Erbium |
| Gd$_2$O$_2$S | Ytterbium | Erbium |
| La$_2$O$_2$S | Ytterbium | Holmium |
| Oxyhalides (OX$_y$) | | |
| YOF | Ytterbium | Thulium |
| Y$_3$OCl$_7$ | Ytterbium | Terbium |
| Fluorides (F$_x$) | | |
| YF$_3$ | Ytterbium | |
| GdF$_3$ | Ytterbium | Erbium |
| LaF$_3$ | Ytterbium | Erbium |
| NaYF$_3$ | Ytterbium | Holmium |
| BaYF$_5$ | Ytterbium | Thulium |
| BaY$_2$F$_8$ | Ytterbium | Thulium |
| Gallates (Ga$_x$O$_y$) | | |
| YGaO$_3$ | Ytterbium | Erbium |
| Y$_3$Ga$_5$O$_{12}$ | Ytterbium | Erbium |
| Silicates (Si$_x$O$_y$) | | |
| YSi$_2$O$_5$ | Ytterbium | Holmium |
| YSi$_3$O$_7$ | Ytterbium | Thulium |

In certain embodiments the coated optical reporter used in the methods of the invention may also comprise at least one electromagnetic emitting material. An electromagnetic emitting material as part of the composition of the invention, allows for the composition to be detected by various methods and devices. Where the electromagnetic emitting material is detectable by mechanical devices which provide at least one source selected from the group consisting of an infrared radiation source, magnetic field source or electromagnetic pulse. This electromagnetic emitting material may be in conjunction with at least one light emitting material, such as an upconverting phosphor.

When the compositions used in the methods of authenticating an article of the invention comprise UCPs, the upconverting phosphor material/particle in certain embodiments have the formula B $$Y_x Yb_y Er_z O_2 S \quad\quad B$$

wherein:

x is from about 0.6 to about 0.95;

y is from about 0.05 to about 0.35; and z is from about 0.1 to about 0.001.

In other embodiments, the upconverting phosphor particle may be of the formula C:

$$Na(Y_x Yb_y Er_z)F_4 \quad\quad C$$

wherein x is from about 0.6 to about 0.95 y is from about 0.05 to about 0.35; and z is from about 0.1 to about 0.001.

In certain embodiments of formula I, L comprises an alkylene moiety having a first end covalently bound to the coated optical reporter particle (cOpR) and a second end covalently bound to the nucleic acid oligomer (NA).

In many embodiments of formula I, L is of the formula D:

$$\text{-A-R}^1\text{-B-} \quad\quad D$$

wherein:

$R^1$ is $C_{2-8}$alkylene;

-A- is a group covalently bonded to the surface of the coated optical reporter; and —B— is a group covalently bonded to the 3' or 5' end of the nucleic acid oligomer.

In certain embodiments of formula D, —$R^1$— is —$(CH_2)_n$— and n is from 2 to 8.

In certain embodiments of formula D, —B— is:

—S—;

—O—;

—$NR^a$—;

—S—$(CH_2)_p$—;

—O—$(CH_2)_p$—;

—$NR^a$—$(CH_2)_p$—;

—S—$(CH_2)_q$—C(O)—$NR^a$—$(CH_2)_p$—;

—O—$(CH_2)_q$—C(O)—$NR^a$—$(CH_2)_p$—;

—$NR^a$—$(CH_2)_q$—C(O)—$NR^a$—$(CH_2)_p$—;

—S—C(O)—$(CH_2)_r$—C(O)—$NR^a$—$(CH_2)_p$—;

—O—C(O)—$(CH_2)_r$—C(O)—$NR^a$—$(CH_2)_p$—; or

—$NR^a$—C(O)—$(CH_2)_r$—C(O)—$NR^a$—$(CH_2)_p$—;

wherein:

p is from 2 to 8;

q is from 1 to 8;

r is from 2 to 8; and each $R^a$ is independently hydrogen or a $C_{1-6}$alkyl.

In certain embodiments of formula D, —B— is:

—S—$(CH_2)_q$—C(O)—$NR^a$—$(CH_2)_p$ or

—$NR^a$—C(O)—$(CH_2)_r$—C(O)—$NR^a$—$(CH_2)_p$—;

wherein:

p is from 2 to 8;

q is from 1 to 8;

r is from 2 to 8; and each $R^a$ is independently hydrogen or a $C_{1-6}$alkyl.

In other embodiments of formula D, —B— is:

—S—$(CH_2)_q$—C(O)—$NR^a$—$(CH_2)_p$ or

—$NR^a$—C(O)—$(CH_2)_r$—C(O)—$NR^2$—$(CH_2)_p$—;

wherein:

p is from 2 to 6;

q is from 1 to 3; and r is 2 or 3.

In other embodiments of formula D, —B— is

—S—$CH_2$—C(O)—NH—$(CH_2)_6$— or

—NH—C(O)—$(CH_2)_3$—C(O)—NH—$(CH_2)_6$—.

In certain embodiments of formula D, -A- is —O—.

In many embodiments of formula I, the coated optical reporter (cOpR) is coated with silica. Usually when the coated optical reporter comprises a coating of silica, the silica comprises at least one Si—O bond.

The value of m in formula I will vary according to the surface area of the coated optical reporter and the number of functional groups on the optical reporter surface cable of bonding to -L-. The value of m is always greater than one, and usually greater than 10. Preferably m is greater than 100, and in many embodiments m is greater than $10^3$. In many embodiments m may be, for example, between about 10 and about $10^9$. In certain embodiments m may be from about 100 to about $10^8$. In some embodiments m may be from about $10^3$ to about $10^7$.

In certain embodiments the compositions used in the methods of the invention are of the formula II:

(UCP)-[A-$R^1$—X—$R^2$—C(O)—$NR^a$—$R^3$-(DNA)]$_m$      II wherein:

m is an integer greater than 1;

UCP is an upconverting phosphor particle;

DNA is a single or double stranded deoxyribonucleic acid oligomer;

-A- is a group capable of covalently bonding to the surface of the Upconverting phosphor particle;

$R^1$ is $C_{2-8}$alkylene, $R^2$ is $C_{1-8}$alkylene or —C(O)—$C_{1-8}$alkylene-;

—X— is —O—, —S— or —$NR^a$—;

$R^3$ is $C_{2-8}$alkylene; and $R^a$ is hydrogen or $C_{1-6}$alkyl.

In certain embodiments of the invention, the subject composition may be of formula III:

(UCP)-[O—$R^1$—X—$R^2$—C(O)—NH—$R^3$-DNA]$_m$      III wherein m, $R^1$, $R^2$, $R^3$, UCP and DNA are as defined herein.

In certain embodiments of the invention, $R^1$ is $C_{2-6}$alkylene.

In certain embodiments of the invention, $R^2$ is $C_{1-6}$alkylene.

In certain embodiments of the invention, $R^3$ is $C_{2-6}$alkylene.

In certain embodiments of the invention, $R^2$ is —C(O)—$C_{2-6}$alkylene-.

In certain embodiments of the invention, $R^1$ is —$(CH_2)_s$— wherein s is from 2 to 6. In some embodiments s is 3.

In certain embodiments of the invention, $R^2$ is —$(CH_2)_t$— wherein t is from 1 to 6. In some embodiments t is 1.

In certain embodiments of the invention, $R^2$ is —C(O)—$(CH_2)_u$— wherein u is from 1 to 6. In some embodiments u is 2 or 3, preferably 2.

In certain embodiments of the invention, $R^3$ is —$(CH_2)_v$— wherein v is from 2 to 6. In some embodiments v is 6.

In certain embodiments of the invention, the subject composition may be of formula IV:

(UCP)-[O—$(CH_2)_s$—S—$(CH_2)_t$—C(O)—NH—$(CH_2)_v$-(DNA)]$_m$      IV wherein:

s is from 2 to 6;

v is from 2 to 6;

t is from 1 to 3; and m, UCP and DNA are as defined herein.

In certain embodiments of the invention, the compositions may be of formula V:

(UCP)-[O—$(CH_2)_s$—NH—C(O)—$(CH_2)_u$—C(O)—NH—$(CH_2)_v$(DNA)]$_m$      V wherein:

s is from 2 to 6;

v is from 2 to 6;

u is 2 or 3; and m, UCP and DNA are as defined herein.

In certain embodiments of the invention, the compositions may be of formula VI:

(UCP)-[O—(CH$_2$)$_3$—S—CH$_2$—C(O)—NH—(CH$_2$)$_6$- (DNA)]$_m$     VI wherein m, UCP and DNA are as defined herein.

In certain embodiments of the invention, the compositions may be of formula VII:

(UCP)-[O—(CH$_2$)$_3$—NH—C(O)—(CH$_2$)$_3$—C(O)— NH—(CH$_2$)$_6$-(DNA)]$_m$     VII wherein m, UCP and DNA are as defined herein.

Optical Reporter Marker Labeling of and Extraction from the Article of Interest

In certain embodiments of the invention, when the article is a textile, the nucleic acid taggant/marker may be mixed with a binder and intergrated into at least one type of thread utilized for manufacturing the textile. The thread can then be utilized to mark or tag the textile itself or a wash/label tag affixed to the textile.

In other embodiments where the article is a textile, the mucleic acid taggant may be applied to the finished textile or wash tag as a fabric paint on a predesignated position on the textile. The fabric paint utilized is formulated to allow detection of an up converting phosphor particle, with minimal quenching of the light emission from the UCP when excited by the appropriate light source.

When the article is a painting, for example, the nucleic acid taggant can be mixed with paints appropriate for the type of painting being marked. The NA taggant is added to the paint mixture at an appropriate concentration to allow for adequate detection of the NA marker. If the NA taggant marker comprises an UCP composition, the paint mixture is compatible with the NA taggant as to not quence the emission of the UCP particle. In some instances, the NA taggant marker may be introduced to the painting as a topcoat or varnish as a topical application on the painting.

When the article is a tablet, such a pharmaceutical drug, the NA taggant marker can be placed or positioned on primary or secondary packaging for the tablet(s). The NA taggant may be applied to the packaging of the tablet as indicia on the packaging or for example, a bar code or SKU number. The ink or paint used as a carrier for the NA taggant is suitable for NA taggant comprising UCP particles, allowing the detection of the location of the NA taggant on the tablet packaging by detecting the phosphorescence from the UCP particle associated with the NA taggant when excited by the correct light source.

When the article mad of metal or plastic for example, the NA marker may be applied to the article in a paint solution. The NA marker can be mixed directly into the paint solution, and then distributed at an appropriate amount onto at least a portion of the solid article. For exemplary purposes, if the article has at least two separate parts, such as a nut and a bolt, the paint solution carrying the NA marker may be placed across both the nut and the bolt, thus insuring the correct parts are being utilized.

In one embodiment, where the NA taggant comprises an up converting particle, the extraction of the NA taggant marker varies depending on if the article being authenticated is a solid or a solution. If the article is of solid form, the NA marker can be located by detecting the presence of the UCP by an appropriate light source. The NA marker can then be extracted from the article by scraping, cutting out, or dissolving the portion of the article which is determined to have the presence of the correct up-converting phosphor particle(s). Once the portion of the article containing the NA marker has been removed the article of interest, the NA marker may isolated and/or prepared for PCR analysis utilizing techniques known to those skilled in the art of PCR sample preparation.

When the article being authenticated is a liquid, such as oil or gasoline, the article can be concentrated to an appropriate amount to allow the detection of the NA marker. When the NA taggant comprises a UCP, the article is concentrated to a predetermined point in which, the UCP emission is detectable by an appropriate light source. The sample may be further treated to allow for the NA taggant in the concentrated sample to prepared for PCR analysis.

Various other types of articles made of metal, plastic, fabric, wood, powder, liquid or other article may be labeled with authenticatable taggants in accordance with the invention. The taggants may be applied to the article in the form of solution, paint, paste, powder, aerosol, or other form, as will be recognized by those skilled in the art.

Kits for Authenticating Articles Using Nucleic Acid-Linked Optical Reporters

The invention also provides kits for authenticating articles of interest using the methods of the invention. The kits of the invention may comprise, for example, a container of the optical reporter marker, and a sample tube for holding a collected sample of the item or article to be authenticated. The kits may further comprise an applicator for applying a sample of the optical reporter to the article. The kits may still further comprise a collection tool for taking a sample of the labeled article for transfer to the sample tube. The kits may further comprise a portable light source for detecting the optical reporters.

By way of example, the optical reporter marker may be in the form of a liquid solution or dispersion, and the container with the kit would be suitably configured for holding a liquid. The applicator of the kit may comprise an "eye-dropper" for applying liquid optical reporter marker solution to the article in droplet form, a spatula for smearing the solution on an article, a syringe for injecting the solution into an article, or like type of applicator. The collection tool of the kit may comprise a spoon, gouge, a scraping or abrading tool for removing a sample of the labeled article, a blade or scissors for cutting a piece of the article, a cloth (which may be solvent-moistened) for wiping a sample from the article, or the like. The sample tube of the kit may comprise a sealable vial or eppendorf tube, and may contain solvent or solution for extraction of the optical reporter marker from the sample taken from the tagged article. The portable light source of the kit may comprise a hand-held UV lamp suitable for detecting the optical reporter marker.

The kit may further comprise primers and/or probes as well as solutions appropriate for PCR analysis. The kit may further comprise a small PCR instrument for analysis of the extracted optical reporter marker.

The kits of the invention thus provide a convenient, portable system for practicing the methods of the invention.

Synthesis of UCP Particles Covalently Linked to Biomolecules

Nucleotide-labeled optical reporters in accordance with the invention can be made by a variety of methods, including those depicted in the co-pending U.S. application "Methods for linking Optical Reporters to Biomolecules," which is herein incorporated by reference.

Preferred methods for preparing UCP particles covalently linked to DNA are provided in the following Examples.

EXAMPLES

The following preparations and examples are given to enable those skilled in the art to more clearly understand and to practice the present invention. They should not be considered as limiting the scope of the invention, but merely as being illustrative and representative thereof.

Up-converting phosphor nanopowder (doped yttrium oxide and yttrium oxysulfide upconverting particles) were obtained from Nanocerox, Inc., Ann Arbor, Mich.

ABBREVIATIONS

UCP Up converting phosphor
UTP Up converting phosphor technology
OpR optical reporter particle
cOpR coated optical reporter particle
TEOS tetraethoxysilane, tetraethyl orthosilicate; ethyl silicate; silicic acid, tetraethyl ester; or silicon ethoxide
MOS methyl oxysilane
EOS ethyl oxysilane
POS propyl oxysiline
NHS N-Hydroxsuccinimde
IOA Iodoacetamide
DIPCI Diisopropylcarbodiimide
DCM dichloromethane/methylene chloride
DIPEA diisopropyl ethylamine
DMF N,N-dimethylformamide
DMAP 4-dimethylaminopyridine
ECDI 1-ethyl-3-(3'-dimethylaminopropyl)carbodiimide
EtOAc ethyl acetate
EtOH ethanol
hplc high performance liquid chromatography
mCPBA m-chloroperbenzoic acid
MeCN acetonitrile
TLC thin layer chromatography

Example 1

Doped Yttrium Oxysulfide with Oxypropylsulfanylacetamide-Linked DNA

The synthetic procedure of this Example is shown below in Scheme A.

SCHEME A

This example demonstrates that the compositions produced by the methods of the inventions, particularly those methods in which nucleotides are linked to a phosphor, that the nucleotide attached to the composition can be detected directly by techniques such as PCR. The phosphor compound utilized in this example was Yttrium oxysulfide up converting particles as well as an amine linked DNA oligomer.

Detection of Bound DNA to Phosphor Articles by Real-Time-PCR.

The equipment and supplies utilized for RT-PCR were the following. PCR capillary system (20 ul capillary) by Roche Diagnostics, LightCycler 2 by Roche Diagnostics, SYBR Green ReadyMix RT-PCR kit by Sigma-Aldrich and SYBR Green JumpStart Taq mix by Sigma.

The following primers were specifically designed for amplification of the DNA oligomer attached to the phosphor particles produced by the methods of the invention. Primer 1-(5'-CGCCAGGGT TTTCCCAGTCACGAC-3') and Primer 2 (5'-CAGGAAACAGCTATGAC-3'). The final concentration of the primers for RT-PCR amplification was 0.05 uM in the RT-PCR rxn sample. The size of the amplicon generated during RT-PCR with this primer pair was approximately 150 bp in length.

The RT-PCR run conditions were as follows. One preheating cycle of 95° C. for 5 minutes, followed by 40 cycles of 20 seconds at 95° C., 40 seconds at the annealing temperature of 50° C., with polymerase extension at 72° C. for 20 seconds.

The isolated phosphor particles containing DNA molecules were resuspended in and diluted 1/10, 1/100, and 1/1000, respectively for RT-PCR analysis. Each RT-PCR sample contained 15 ul of RT-PCR master mix 0.5 ul of each Primer stock solution, 1 ul of a specified diluted phosphor containing DNA sample, and 13 ul water were mixed and put into 20 ul capillary tubes. Positive and Negative controls were also prepared. Duplicates of all RT-PCR samples were prepared and analyzed.

The results from the RT-PCR experiment where similar to those shown in FIG. 2, discussed below in Example 2.

Example 2

Doped Yttrium Oxysulfide with (oxy-propylamino)-acetic acid 5-amino-4-oxo-pentyl Ester-Linked DNA

The synthetic procedure of this example is shown below in Scheme B.

SCHEME B

-continued

This example demonstrates that the compositions produced by the methods of the inventions, particularly those methods in which nucleotides are linked to a phosphor, that the nucleotide attached to the composition can be detected directly by techniques such as PCR. The phosphor compound utilized in this example was Yttrium oxysulfide up converting particles as well as an amine linked DNA oligomer.

Detection of Bound DNA to Phosphor Particles by Real-Time-PCR.

The equipment and supplies utilized for RT-PCR were the following. PCR capillary system (20 ul capillary) by Roche Diagnostics, LightCycler 2 by Roche Diagnostics, SYBR Green ReadyMix RT-PCR kit by Sigma-Aldrich and SYBR Green JumpStart Taq mix by Sigma.

The following primers were specifically designed for amplification of the DNA oligomer attached to the phosphor particles produced by the methods of the invention. Primer 1-(5'-CGCCAGGGT TTTCCCAGTCACGAC-3') and Primer 2 (5'-CAGGAAACAGCTATGAC-3'). The final concentration of the primers for RT-PCR amplification was 0.05 uM in the RT-PCR rxn sample. The size of the amplicon generated during RT-PCR with this primer pair was approximately 150 bp in length.

The RT-PCR run conditions were as follows. One preheating cycle of 95° C. for 5 minutes, followed by 40 cycles of 20 seconds at 95° C., 40 seconds at the annealing temperature of 50° C., with polymerase extension at 72° C. for 20 seconds.

The isolated phosphor particles containing DNA molecules were resuspended in and diluted $1/10$, $1/100$, and $1/1000$, respectively for RT-PCR analysis. Each RT-PCR sample contained 15 ul of RT-PCR master mix 0.5 ul of each Primer stock solution, 1 ul of a specified diluted phosphor containing DNA sample, and 13 ul water were mixed and put into 20 ul capillary tubes. Positive and Negative controls were also prepared. Duplicates of all RT-PCR samples were prepared and analyzed.

Figure 2:
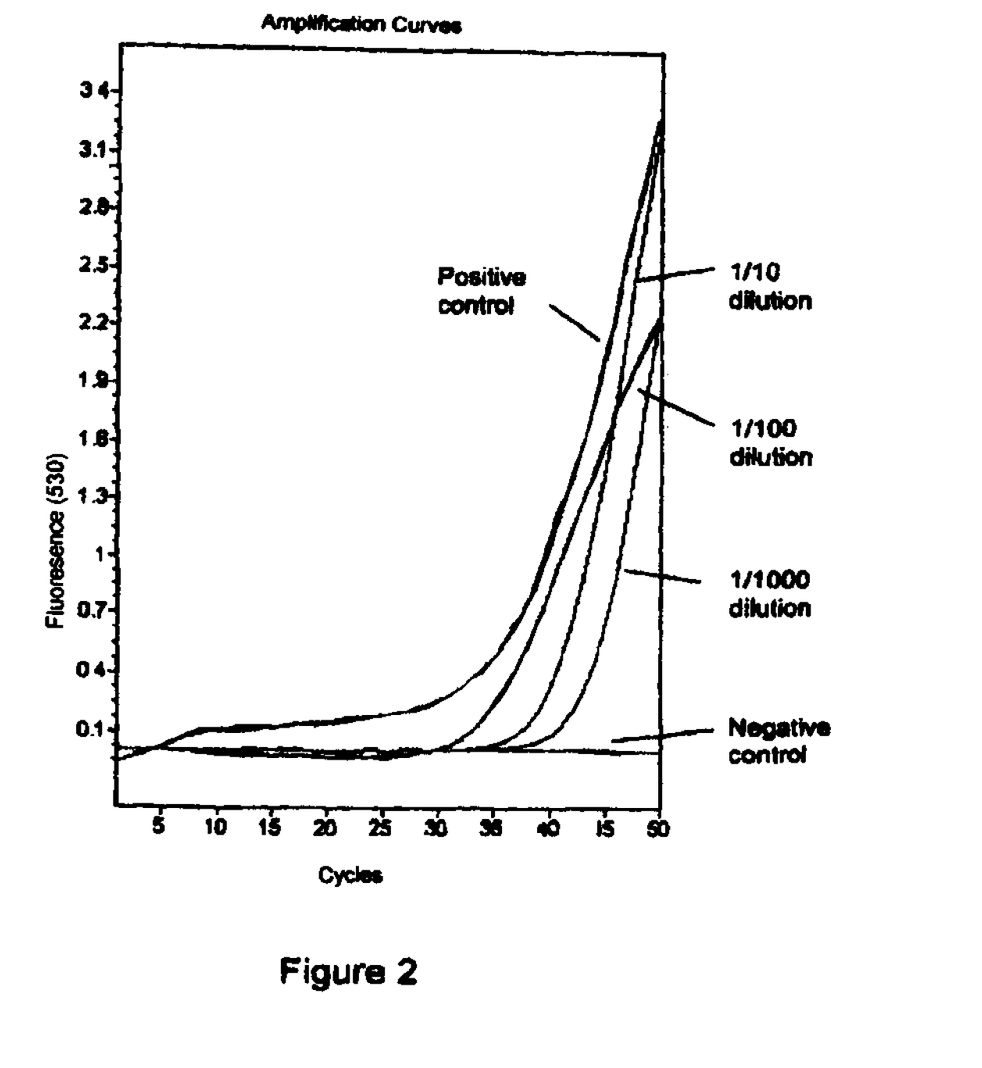
FIG. 2 is a plot of a real-time PCR results for a composition of the invention, comprising an optical reporter linked to a sequenceable DNA molecule.

The results from the RT-PCR experiment are shown in FIG. 2. The results in FIG. 2 show that the $1/100$ dilution sample had a Ct of 30, while the $1/10$ and $1/1000$ dilution had a Ct of 33 and Ct of 36, respectively. At the $1/10$ dilution the concentration of the UCP particles is high enough to quench the PCR signal, thus delaying the cycle in which amplification of the target DNA is present.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method for authenticating an article comprising the steps of: providing an optical reporter marker, the optical reporter marker having at least one light emitting upconverting phosphor particle linked by a linking group comprising an alkylene moiety, to a nucleic acid taggant, the nucleic acid taggant having a plurality of artificial polymorphic double stranded (ds) DNA fragments, said artificial polymorphic dsDNA fragments each having an artificial sequence obtained by restriction digestion and ligation of extracted DNA applying the optical reporter marker onto the article of interest, detecting the optical reporter marker associated with the article of interest with a light source, obtaining a sample of the optical reporter marker from the article of interest for analysis;

analyzing the collected sample to detect the presence of the identifiable portion of the artificial polymorphic double stranded (ds)DNA fragments linked to the upconverting phosphor particle using a polymerase chain reaction-on the collected sample comprising said artificial polymorphic (ds)DNA fragments using specific primers, thereby producing specific length amplicons; and verifying that the article is genuine by detecting the specific length amplicons amplified from said artificial polymorphic dsDNA fragments on said article of interest, wherein verifying that the article is genuine by detecting said polymorphic DNA fragments in said article comprises analyzing the specific lengths of said specific length amplicons.

2. The method of claim 1, wherein the optical reporter marker has the composition of the formula I:

wherein:

m is an integer greater than 1;

(cOpR) is a coated optical reporter particle, said (cOpR) having an upconverting phosphor (UCP) material;

(NA) is a nucleic acid oligomer of detectable sequence, wherein (NA) is a double stranded DNA molecule having a length of between 100 base pairs and 800 base pairs; and L is said linking group covalently bound to the coated optical reporter particle and to the nucleic acid oligomer, wherein L comprises said alkylene moiety.

3. The method of claim 2, wherein (UCP) is an upconverting phosphor particle of the formula:

wherein:

x is from about 0.6 to about 0.95;

y is from about 0.05 to about 0.35; and z is from about 0.1 to about 0.001.

4. The method of claim 2, wherein L is of the formula:

wherein:

$R^1$ is $C_{2-8}$alkylene;

-A- is a group covalently bonded to the surface of the coated optical reporter; and —B— is a group covalently bonded to the 3' or 5' end of the nucleic acid oligomer.

5. The method of claim 4, wherein -A- is —O—.

6. The method of claim 4, wherein —$R^1$— is —$(CH_2)_n$— and wherein n is from 2 to 8.

7. The method of claim 4, wherein

—S—;

—O—;

—NRa-;

—S—(CH$_2$)$_p$—;

—O—(CH$_2$)$_p$—;

—NR$^a$—(CH$_2$)$_p$—;

—S—(CH$_2$)$_q$—C(O)—NR$^a$—(CH$_2$)$_p$—;

—O—(CH$_2$)$_q$—C(O)—NR$^a$—(CH$_2$)$_p$—;

—NR$^a$—(CH$_2$)$_q$—C(O)—NR$^a$—(CH$_2$)$_p$—;

—S—C(O)—(CH$_2$)$_r$—C(O)—NR$^a$—(CH$_2$)$_p$—;

—O—C(O)—(CH$_2$)$_r$—C(O)—NR$^a$—(CH$_2$)$_p$—; or

—NR$^a$—C(O)—(CH$_2$)$_r$—C(O)—NR$^a$—(CH$_2$)$_p$—;

wherein:
p is from 2 to 8;
q is from 1 to 8;
r is from 2 to 8; and
each R$^a$ is independently hydrogen or C$_{1-6}$alkyl.

8. The method of claim 4, wherein —B— is:

—S—(CH$_2$)$_q$—C(O)—NR$^a$—(CH$_2$)$_p$ or

—NR$^a$—C(O)—(CH$_2$)$_r$—C(O)—NR$^a$—(CH$_2$)$_p$—;

wherein
p is from 2 to 8;
q is from 1 to 8;
r is from 2 to 8; and
each R$^a$ is independently hydrogen or C$_{1-6}$alkyl.

9. The method of claim 8, wherein:
p is from 2 to 6;
q is from 1 to 3; and
r is 2 or 3.

10. The method of claim 4, wherein —B— is:

—S—CH$_2$—C(O)—NH—(CH$_2$)$_6$—; or

—NH—C(O)—(CH$_2$)$_3$—C(O)—NH—(CH$_2$)$_6$—.

11. The method of claim 2, wherein the cOpR is coated with silica.

12. The method of claim 11, wherein the cOpR is a coated optical reporter particle having an upconverting phosphor (UCP) material comprising Yttrium oxysulfide.

13. The method of claim 1, wherein the optical reporter marker has the composition of the formula II:

(UCP)-[A-R$^1$—X—R$^2$—C(O)—NR$^a$—R$^3$-(DNA)]$_m$   II wherein:
m is an integer greater than 1;
UCP is an upconverting phosphor particle;
DNA is a single or double stranded deoxyribonucleic acid oligomer;
-A- is a group capable of covalently bonding to the surface of the Upconverting phosphor particle;
R$^1$ is C$_{2-8}$alkylene,
R$^2$ is C$_{1-8}$alkylene or —C(O)—C$_{1-8}$alkylene-;
—X— is —O—, —S— or —NR$^a$—;
R$^3$ is C$_{2-8}$alkylene; and
R$^a$ is hydrogen or C$_{1-6}$alkyl.

14. The method of claim 13, wherein the optical reporter composition is of the formula IV:

(UCP)-[O—(CH$_2$)$_s$—NH—C(O)—(CH$_2$)$_t$—C(O)—NH—(CH$_2$)$_v$-(DNA)]$_m$   IV wherein:
s is from 2 to 6;
v is from 2 to 6; and
t is from 1 to 3.

15. The method of claim 13, wherein the optical reporter composition is of the formula V:

(UCP)-[O—(CH$_2$)$_s$—NH—C(O)—(CH$_2$)$_u$—C(O)—NH—(CH$_2$)$_v$-(DNA)]$_m$   V wherein:
s is from 2 to 6;
v is from 2 to 6; and
u is 2 or 3.

16. The method of claim 13, the optical reporter composition is of the formula VI:

(UCP)-[O—(CH$_2$)$_3$—S—CH$_2$—C(O)—NH—(CH$_2$)$_6$-(DNA)]$_m$   VI.

17. The method of claim 13, wherein the optical reporter composition is of the formula VII:

(UCP)-[O—(CH$_2$)$_3$—NH—C(O)—(CH$_2$)$_3$—C(O)—NH—(CH$_2$)$_6$-(DNA)]$_m$   VII.

18. The composition of claim 2, wherein the cOpR comprises a visually detectable light emitting material selected from the group consisting of a fluorescent dye, a upconverting phosphor, a rare earth-doped ceramic powder, and a quantum dot.

19. The composition of claim 18, where said light emitting material is excitable by UV light or infrared light.

20. The method of claim 2, wherein the cOpR comprises at least one electromagnetic radiation emitting material.

21. The composition of claim 20, where the electromagnetic emitting material is detectable by a device which provides a source selected from the group consisting of an infrared radiation source, a magnetic field source, a quantum dot and an electromagnetic pulse source.

22. The method of claim 1, wherein the article is selected from the group consisting of a manufactured good, a painting, a painting and frame, a monetary paper, an ink, a fabric, a metal machined part, a CD-ROM, a tablet, and an electronic part.

23. The method of claim 1, wherein the optical reporter marker applied to the article is associated with a database management system, wherein the database management system associates the optical reporter marker with said article.

24. A method for authenticating a particular good, comprising: providing a optical reporter marker linked by a linking group comprising an alkylene moiety, to at least one nucleic acid taggant, the nucleic acid taggant having a plurality of polymorphic double stranded (ds) DNA fragments, said plurality of polymorphic double stranded (ds) DNA fragments each having an artificial sequence obtained by restriction digestion and ligation of extracted DNA and having an identifiable portion;

applying the optical reporter marker to at least one particular good, wherein the good enters at least one supply chain;

locating and collecting a sample of the optical reporter marker from said particular good after said particular good has entered said supply chain; and identifying said nucleic acid taggant in said particular good by identifying one or more of said plurality of polymorphic dsDNA fragments in said particular good and thereby authenticating the particular good as genuine.

25. A kit for authenticating articles comprising:
a container containing an optical reporter marker, the optical reporter marker having at least one light emitting upconverting phosphor particle linked by a linking group comprising an alkylene moiety, to a nucleic acid taggant, the nucleic acid taggant having a plurality of artificial polymorphic double stranded (ds) DNA fragments, said plurality of artificial polymorphic dsDNA fragments each having an artificial sequence obtained by restriction digestion and ligation of extracted DNA; and
an applicator for applying the optical reporter marker to the article.

26. A method for authenticating an article comprising the steps of:
providing an article having an optical reporter marker, the optical reporter marker having at least one light emitting upconverting phosphor particle covalently linked by a linking group comprising an alkylene moiety, to a nucleic acid taggant, the nucleic acid taggant having a plurality of polymorphic DNA fragments, said polymorphic DNA fragments each having an artificial sequence obtained by digestion and ligation of extracted DNA and having an identifiable portion,
applying the optical reporter marker to the article,
detecting the optical reporter marker associated with the article with a light source,
obtaining a sample of the optical reporter marker from the article for analysis,
analyzing the collected sample to detect the presence of the identifiable portion of the polymorphic DNA fragments covalently linked to the upconverting phosphor particle by performing a polymerase chain reaction (PCR) using specific primers to produce amplicons of a specific length; and
verifying that the article is genuine by detecting said specific amplicons by length.

27. The method of claim 1, wherein verifying that the article is genuine by detecting said polymorphic DNA fragments in said article comprises analyzing the specific lengths of said specific length amplicons by capillary electrophoresis.

28. The method of claim 1, wherein said polymorphic DNA fragments are non-heritable.

29. The method of claim 22, wherein said article is a painting or a painting and frame.

30. The method of claim 24, wherein said identifying one or more of said plurality of polymorphic dsDNA fragments is by detecting specific length amplicons amplified from said one or more polymorphic DNA fragments.

31. The method of claim 30, wherein said detecting specific length amplicons amplified from said one or more polymorphic DNA fragments is by capillary electrophoresis.

32. The kit according to claim 25, further comprising a light source suitable for detecting the optical reporter.

33. The kit according to claim 25, further comprising a collection tool for taking a sample from the article.

34. The method of claim 26, wherein said detecting said specific amplicons by length is by capillary electrophoresis.

* * * * *